United States Patent [19]

Grover et al.

[11] Patent Number: 5,354,764

[45] Date of Patent: Oct. 11, 1994

[54] METHOD FOR INHIBITING MYOCARDIAL CELL NECROSIS AND PRESERVING HEART FUNCTION DURING MYOCARDIAL ISCHEMIA AND/OR REPERFUSION

[75] Inventors: Gary J. Grover, Stockton, N.J.; Karnail Atwal, Newtown, Pa.

[73] Assignee: E. R. Squibb & Sons, Inc., Princeton, N.J.

[21] Appl. No.: 970,753

[22] Filed: Nov. 2, 1992

Related U.S. Application Data

[60] Division of Ser. No. 784,482, Oct. 29, 1991, Pat. No. 5,256,688, which is a continuation-in-part of Ser. No. 411,137, Sep. 22, 1989, abandoned, which is a continuation-in-part of Ser. No. 220,886, Jul. 18, 1988, abandoned.

[51] Int. Cl.$^5$ .............................................. A61K 31/44
[52] U.S. Cl. ..................................................... 514/353
[58] Field of Search ......................................... 514/353

[56] References Cited

PUBLICATIONS

G. J. Gross et al, Journal of Cardiov. Pharm., 10(Suppl.8): S76–S84 (1987).
Norio Taira, Journal of Cardiov. Pharm., 10(Suppl.8):-S1–S9 (1987).
Naoaki Imai et al, Circulation, vol. 77, No. 3, Mar. 1988, pp. 705–710.
Nigel S. Cook, TIPS, Jan. 1988 (vol. 9) pp. 21–28.
Sakamoto et al, CA 105:91027q (1986).
Sakamoto et al, J. Nihon Univ. Med. Ass., vol. 45, No. 4, pp. 299–307, 1986.

*Primary Examiner*—Zohreh Fay
*Attorney, Agent, or Firm*—Burton Rodney

[57] ABSTRACT

A method is provided for inhibiting myocardial cell necrosis and improving myocardial function during myocardial ischemia and/or reperfusion by locally administering to the heart a potent potassium channel activator such as pinacidil or cromakalim.

7 Claims, 5 Drawing Sheets

METHOD FOR INHIBITING MYOCARDIAL CELL NECROSIS AND PRESERVING HEART FUNCTION DURING MYOCARDIAL ISCHEMIA AND/OR REPERFUSION

REFERENCE TO PRIOR APPLICATION

This is a division of U.S. patent application Ser. No. 784,482, filed Oct. 29, 1991, now U.S. Pat. No. 5,256,688 which is a continuation-in-part of U.S. patent application Ser. No. 411,137, filed Sep. 22, 1989, now abandoned which is a continuation-in-part of U.S. patent application Ser. No. 220,886, filed Jul. 18, 1988, now abandoned.

FIELD OF THE INVENTION

The present invention relates to a method for inhibiting myocardial cell necrosis and improving myocardial function in mammalian species during myocardial ischemia and/or reperfusion by administering a potent potassium channel activator, locally to the heart, to enhance the recovery of heart function.

BACKGROUND OF THE INVENTION

Blood flow reductions in the heart can result in dysfunction of this organ and cell death if the flow reduction is severe enough. Restoration of coronary blood flow early during a heart attack is becoming a clinical reality with the advent and improvements in thrombolytic, mechanical, and surgical interventions. While early restoration of blood flow, for example, by thrombolysis or following transient ischemia, can prevent or mitigate the degree of cell death (infarction) occurring, reperfusion can still be associated with some degree of cardiac dysfunction or cell death (also referred to as stunned myocardia), a process begun during ischemia. Thus, it would be of great clinical value to find a means to preserve reperfusion function or cell viability of the heart and one means of doing this is to reduce the severity of ischemia before reperfusion.

Recently, a new class of compounds has been described and labeled potassium channel activators (PCA), Cook, N. S. "The pharmacology of potassium channels and their therapeutic potential," TIPS 9:21, 1988. Cook indicates "that the cellular site of action of a number of drugs used therapeutically seems to involve the modulation of membrane K[+] channels" and that "opening of K[+] channels by a new class of drugs appears to underlie their relaxation of a variety of smooth muscles" because of their ability to hyperpolarize and thus relax these cells.

Examples of such PCA drugs or compounds include (+)-2-cyano-1-(4-pyridyl)-3-(1,2,2-trimethylpropyl)-guanidine (hereinafter referred to as pinacidil) and (±)-6-cyano-3,4-dihydro-2,2-dimethyl-trans-4-(2-oxo-1-pyrrolidyl)-2H-benzo[b]-pyran-3-ol (hereinafter referred to as cromakalim or BRL 34915).

Other examples of compounds which are potassium channel activators but which have substantially weaker PCA activity include N-(2-hydroxyethyl)nicotinamide nitrate ester (hereinafter referred to as nicorandil) and 6-amino-1,2-dihydro-1-hydroxy-2-imino-4-piperidino-pyrimidine (hereinafter referred to a minoxidil).

The above PCA compounds have been found to reduce blood pressure and thus may be useful as antihypertensive agents.

Sakamoto et al, Chem. Abst. 105:91027q (1986) which is based on the complete paper found in J. Nihon Univ. Med. Ass., Vol. 45, No. 4, pp 299–307 (1986), show that pinacidil administered systemically reduces arterial blood pressure in dogs subjected to myocardial ischemia, and that cardiac output increases in dogs given pinacidil compared to control animals, though contractility (function) of the heart itself is not improved as LV dp/dt is not improved. Thus, it appears that cardiac output is improved because blood pressure is reduced and thus the heart can more easily pump blood.

Imai, N., et al, "Comparative effects of nitroprusside and pinacidil on myocardial blood flow and infarct size in awake dogs with acute myocardial infarction." Circulation 77:705, 1988, discloses that pinacidil, a coronary vasodilator, given systemically, has no effect on either blood flow to ischemic myocardium or infarct size. Gross, G. J., et al, "Comparative Effects of Nicorandil, Nitroglycerin, Nicotinic Acid and SG-86 on the Metabolic Status and Functional Recovery of the Ischemic-Reperfused Myocardium, J. Cardiovascular Pharmacology, 10 (Suppl. 8):S76–S84 (1987), disclose that "nicorandil and nicotinic acid infusion prior to and during a 15-min coronary occlusion resulted in a significantly improved recovery of mycocardial segment function (%SS, dL/dt) during a 3-h reperfusion period . . . ." However, blood flow was more homogeneously distributed between ischemic and nonischemic regions following nicorandil treatment during reperfusion . . . ." (page S83). It is believed that nicorandil's improvement of post-ischemic function is probably due to its nitrate-like action (for instance like nitroglycerin) and not due to its weak potency as a potassium channel activator (Taira, N., "Similarity and Dissimilarity in the Mode and Mechanism of Action between Nicorandil and Classical Nitrates: An Overview", J. Cardiovascular Pharmacology, 10 (Suppl. 8):S1–S9 (1987).

DESCRIPTION OF THE INVENTION

In accordance with the present invention, a method is provided for inhibiting myocardial cell necrosis and improving myocardial function in mammalian species during myocardial ischemia and/or reperfusion to improve heart function, wherein a therapeutically effective amount of a potent potassium channel activator is administered locally to the heart, that is to the coronary arteries, for example, by catheter, by intracoronary injection or by cardioplegic solution by the aortic route, prior to, during or after reperfusion.

The term "reperfusion" is employed herein to refer to release of occlusion and resumption of blood flow.

It has been found that the potent potassium channel activator improves performance of the heart during and after myocardial ischemia when administered during both the coronary occlusion period and the reperfusion period or only during the reperfusion period. Such improvement in performance of the heart is evidenced by decreased contractile dysfunction and decrease in tissue necrosis (as measured by lactate dehydrogenase release).

Potassium channel activators which are suitable for use herein are those which exhibit potent inhibition of spontaneous mechanical activity in rat portal vein as described hereinafter, that is, an $IC_{50}$ (50% of the maximum inhibition) of less than 2 $\mu M$. Examples of such potassium channel activators suitable for use herein include cromakalim which has an $IC_{50}$ of about 0.12 $\mu M$ and pinacidil which as an $IC_{50}$ of about 0.15 $\mu M$.

DETAILED DESCRIPTION OF THE INVENTION

In carrying out the method of the present invention, the potassium charmel activator may be administered to mammalian species, such as monkeys, dogs, cats, rats, humans, etc. during the period of myocardial ischemia (for example, during coronary occlusion), and reperfusion, and/or during the ischemic attack, and within 1 to 2 hours after the ischemia.

The potassium channel activator may be administered locally to the heart, such as locally to the coronary arteries, by catheter such as by arterial angiography, intracoronary injection or in a cardioplegic solution by the aortic route (retrograde) as employed in cardiopulmonary bypass procedures.

With regard to dosage of potassium channel activator, where the drug is administered by arterial angiography or intracoronary injection, from about 0.001 to about 30 mg/kg/treatment and preferably from about 0.5 to about 25 mg/kg/treatment will be employed. Where the drug is administered in a cardioplegic solution by the aortic route, solutions of drug in cold cardioprotective salt solutions will be employed to provide drug in an amount of from about 0.001 to about 30 mg/kg/treatment and preferably from about 0.5 to about 25 mg/kg/treatment. The number of treatments will depend upon the length of the ischemic attack and the progress of reperfusion to achieve normal heart function. Usually, from 1 to 5 treatments per day will be required for as long as contractile dysfunction continues.

Where the potassium charmel activator is to be administered by angiography or intracoronary injection, it will be formulated in a conventional vehicle, such as distilled water, saline, Ringer's solution, or other conventional carriers. Conventional cardioplegic solutions may be employed as carriers which will contain potassium salts, sodium salts, magnesium salts and possibly calcium salts as will be apparent to those skilled in the art.

REFERENCE TO ACCOMPANYING FIGURES

Figure 3A:
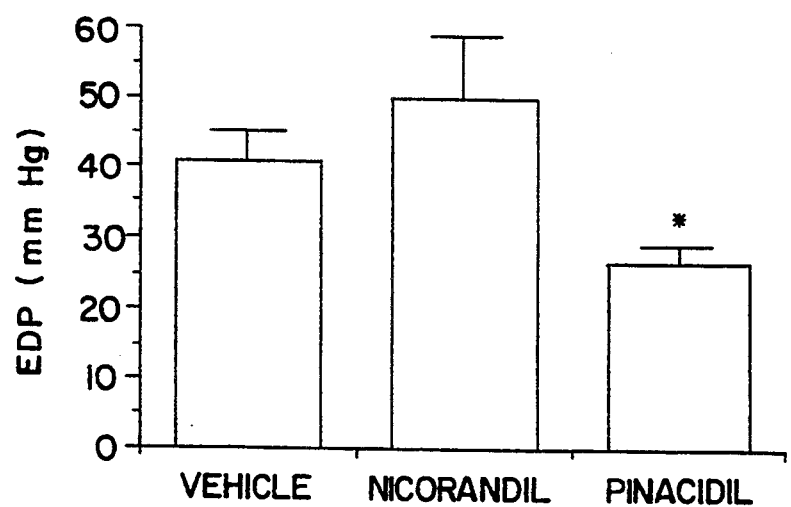
Figure 3B:
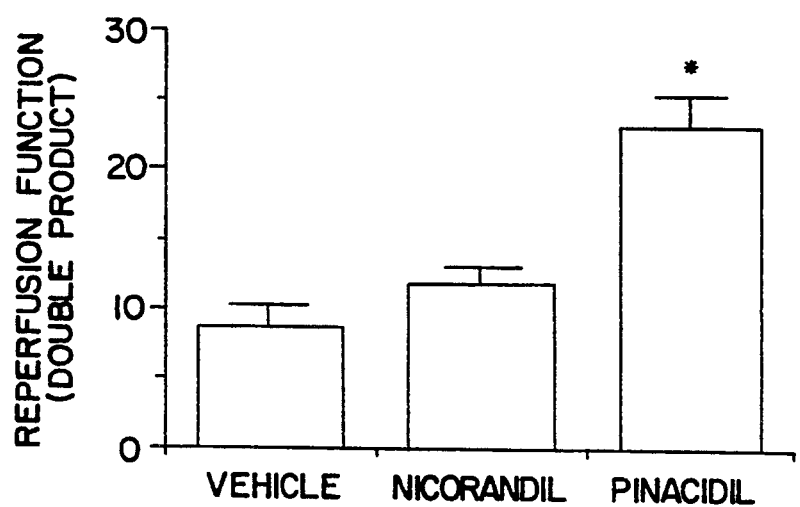
Figure 3C:
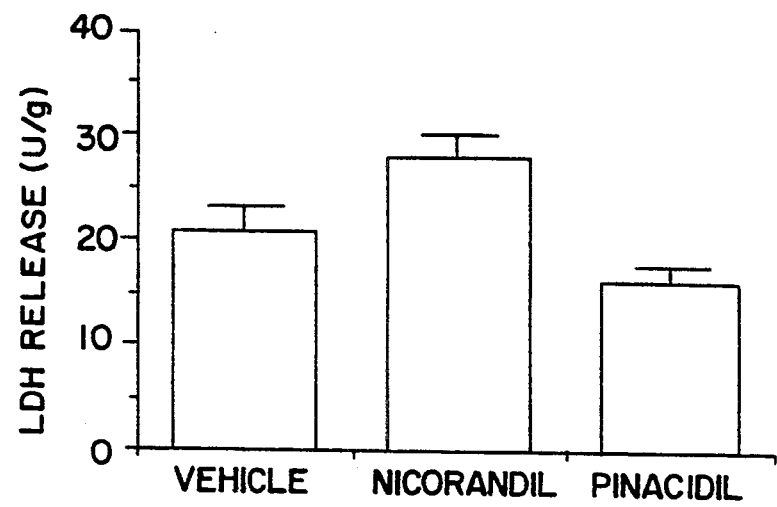
Figure 4A:
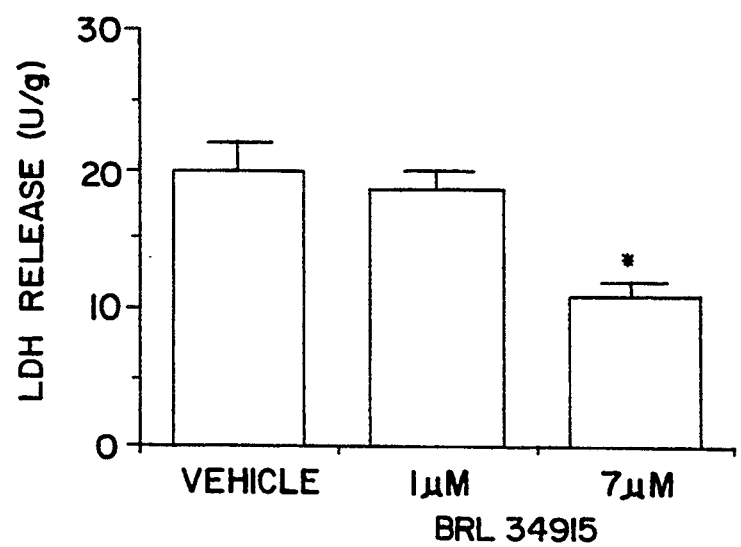
Figure 4B:
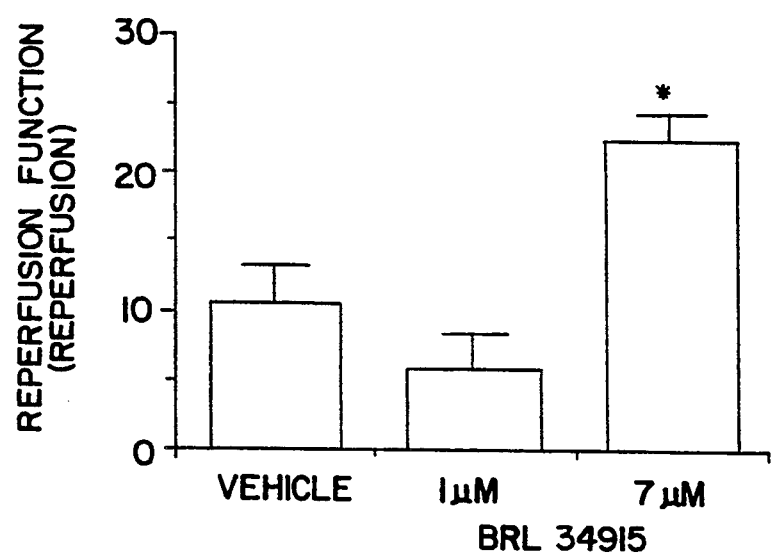
Figure 5A:
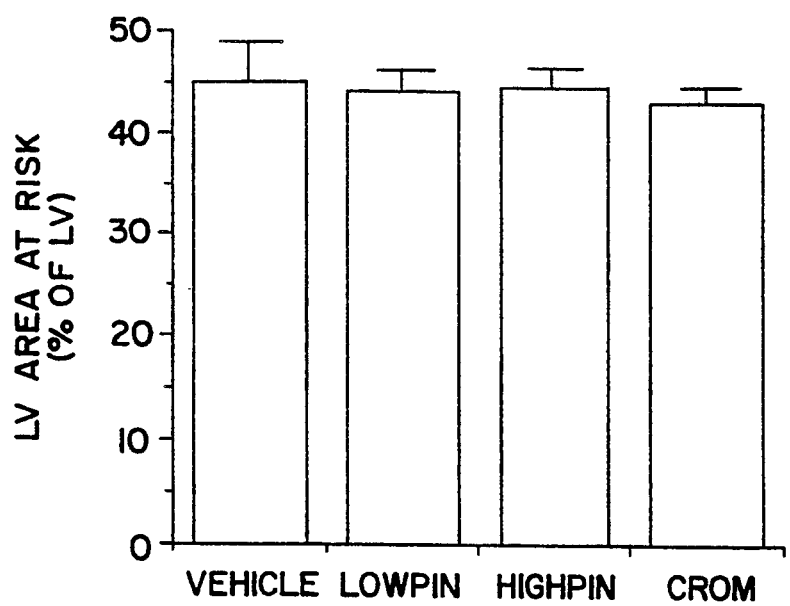
Figure 5B:
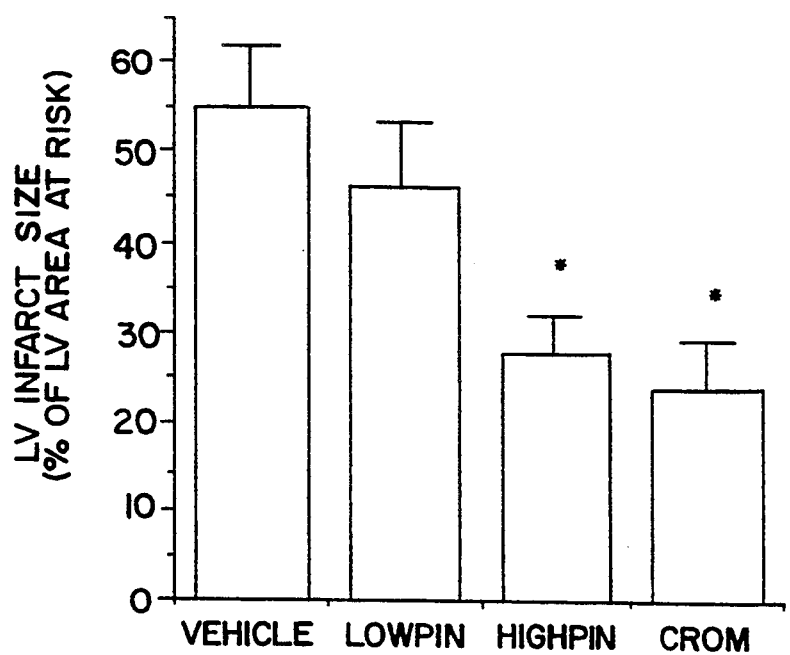
Figure 6A:
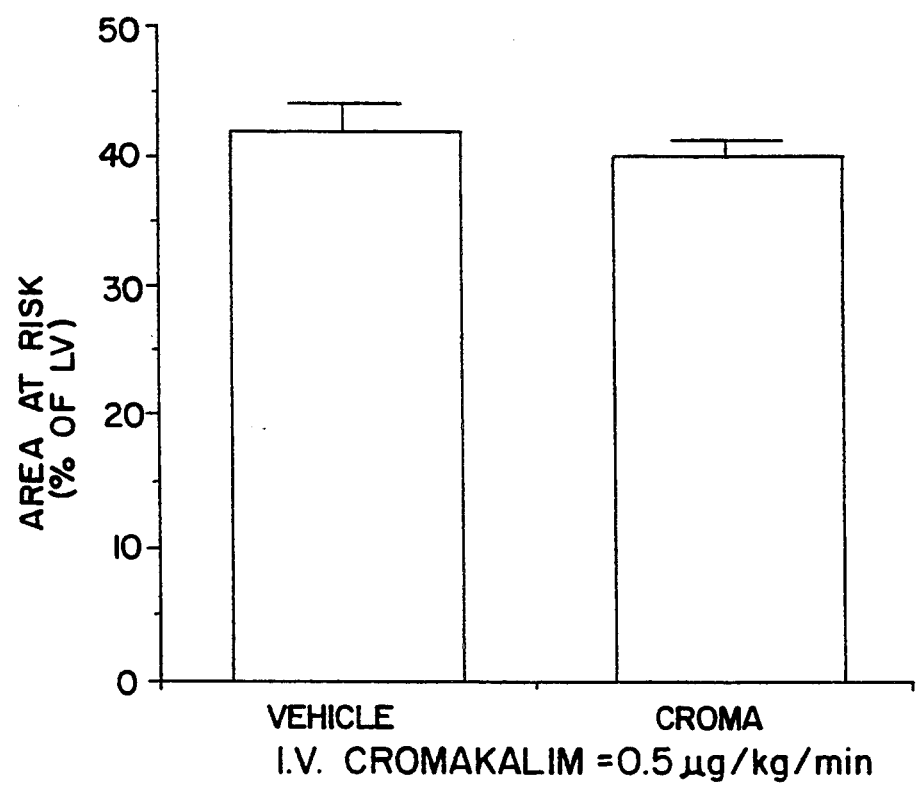
Figure 6B:
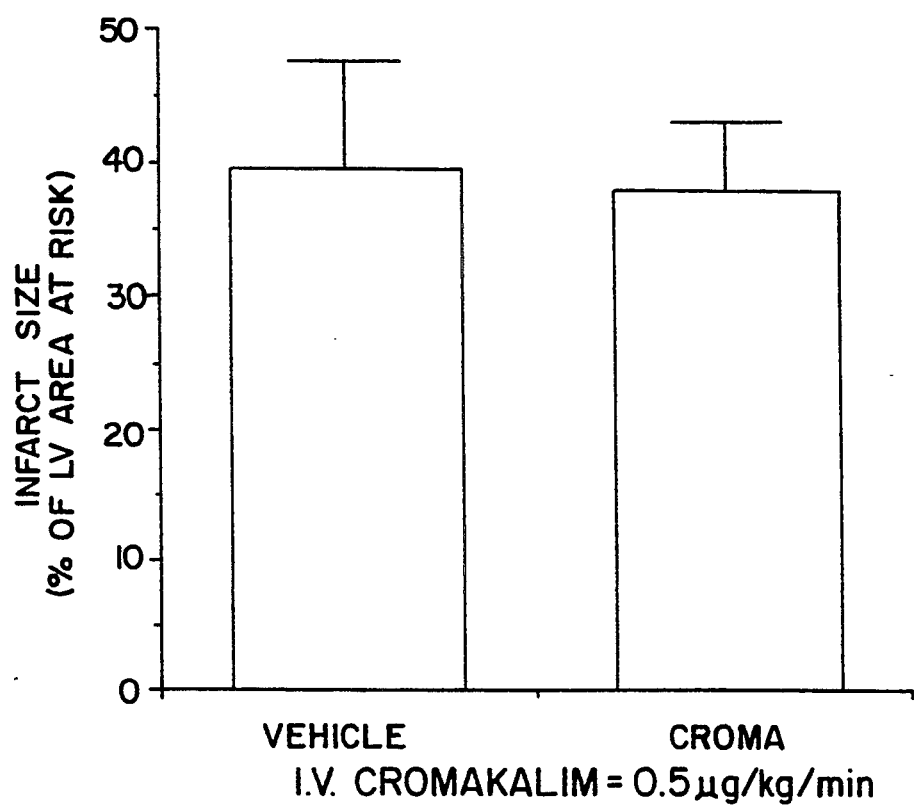

FIGS. 3a 3b and 3c, are graphs of end diastolic pressure (EDP), reperfusion function and lactate dehydrogenase (LDH) release for each of vehicle, nicorandil and pinacidil;

FIG. 4a and 4b are graphs of lactate dehydrogenase (LDH) release and reperfusion function for each of vehicle and cromakalim (BRL 34915) at concentrations of 1μM and 7 μM;

FIG. 5a and 5b are graphs which show the effect of 0.1 μg/kg/min cromakalim (CROM) or 0.09 and 0.90 μg/kg/min pinacidil (LOWPIN and HIGHPIN, resp.) given i.c. starting 10 minutes before left circumflex coronary (LCX) occlusion on myocardial infarct size. The LV (left ventricular) areas at risk are also shown on this Figure and as can be seen, no differences between groups were noted; and FIG. 6a and 6b are graphs which show the effect of i.v. cromakalim (CROMA) on myocardial infarct size as a percent of the left ventricular (LV) area of risk.

EXAMPLE A

Design of In Vitro Screen for Identification of "Potent" Potassium Channel Activators Suitable for Use Herein Methods Solutions:

A bicarbonate buffered physiological (cardioplegic) salt solution (PSS) was used containing, in mM: 118.4 NaCl, 4.7 KCl, 1.2 $KH_2PO_4$, 1.2 $MgSO_4$, 2.5 $CaCl_2$, 25.0 $NaHCO_3$ and 11.7 glucose. PSS with varying concentrations of KCl was prepared by addition of appropriate amounts of KCl from a 4M KCl stock. Calcium free PSS was prepared by deletion of $CaCl_2$ and addition of 1.0 mM [ethylenebis(oxyethylenenitrilo)]-tetraacetic acid (EGTA). All solutions were aerated with 95% $O_2$—5% $CO_2$ such that the pH was 7.4. Experiments were conducted at 37° C.

Stock solutions of test compounds were prepared daily. The compounds were dissolved in water or DMSO as appropriate.

Tissue Preparation:

Normotensive male Wistar Kyoto rats approximately 14 weeks old were sacrificed using $CO_2$. The thoracic aorta and portal vein were quickly removed and placed into cold PSS. Blood was rinsed from the lumen and adherent connective tissue was carefully removed. Rings approximately 4 mm in width were cut from each aorta. The endothelium was mechanically removed by inserting a wire into the lumen and gently rolling the ring on filter paper moistened with PSS. The aortic rings were mounted on stainless steel tissue wires attached to tissue holders. An intact segment of portal vein extending approximately 2 cm from the liver hilus was mounted longitudinally on tissue holders. The tissues were suspended in individual 20 ml organ chambers and connected to a micrometer for control of tissue length and a Grass FT.03 force transducer. Mechanical responses were recorded on Grass Model 7D polygraphs.

The following compounds were tested.

TABLE 1

| Primary mechanisms of action of vasodilators. ||
|---|---|
| Mechanism of Action | Compounds Tested |
| Potassium channel activation | Chromakalim (BRL 34915), pinacidil, nicorandil, minoxidil, minoxidil sulfate, (trans)-4-amino-3,4-dihydro-3-hydroxy-2,2-dimethyl-2H-1-benzopyran-6-carbonitrile (SQ 32,844) |
| Guanylate cyclase activator | Na nitroprusside, nicorandil, 8-Br cyclic GMP |

Experimental Protocol

The rat portal vein segments were gradually stretched over a 1 to 2 hour eguilibration period to a preload of 0.5 g. When the frequency and height of the spontaneous twitches had stabilized, propranolol (1 μM) was added and cumulative concentration response curves were obtained for the test compounds. A steady state reduction of the twitch height and frequency was reached before the next concentration was added.

Evaluation of Results

Force development by the portal vein segments was determined at the peak of the twitch. The effect of each compound on force was calculated relative to the force in its absence. $IC_{50}$ values were determined at the concentration where 50% of the maximal inhibition force was attained. In addition, the relative frequency of twitches was determined by counting the number of twitches in a 5 minute period following drug addition and determining the change in rate from basal (absence of test compound). Results were then calculated as % inhibition of twitch frequency. Data are reported as mean±SEM.

Results

Figure 1:
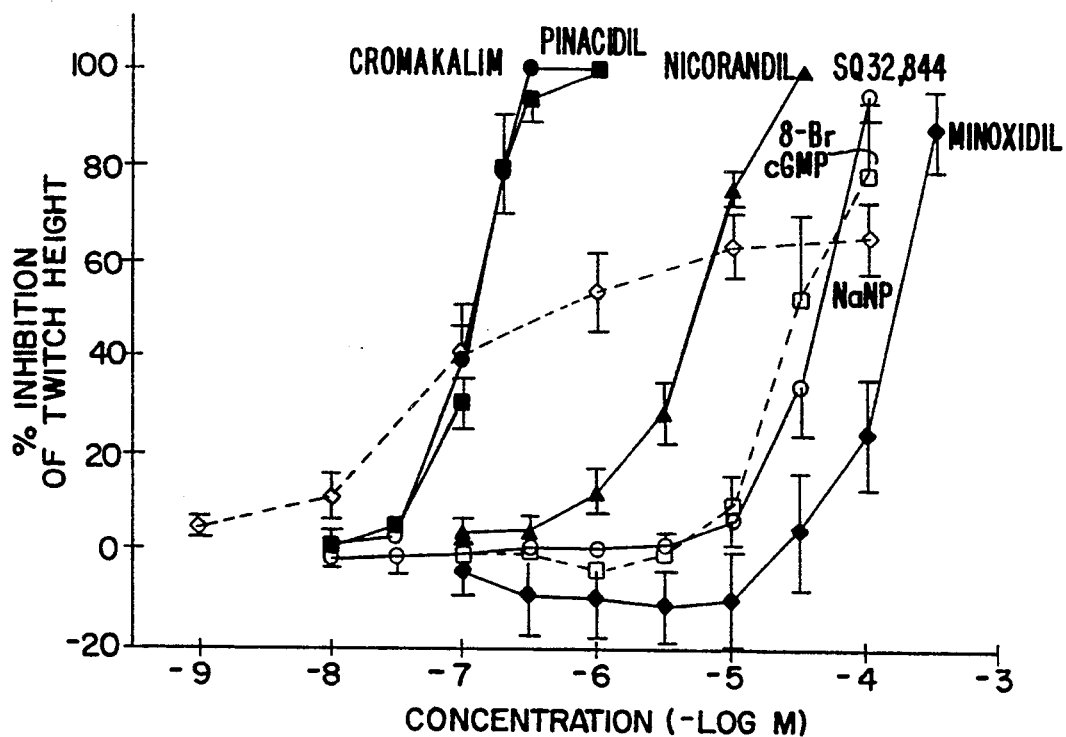
FIG. 1 is a graph of the cumulative concentration response curves for inhibition of spontaneous force development in rat portal veins.

Responses in rat portal vein:

The potassium channel activators inhibited the spontaneous mechanical response in rat portal vein in a concentration dependent manner (Table II and FIG. 1). The spontaneous mechanical activity in the portal vein was slightly more sensitive to cromakalim and pinacidil than were the phenylephrine contractions in the aorta. The portal vein was less sensitive to nicorandil and sodium nitroprusside. Additionally, sodium nitroprusside did not completely inhibit the twitch height even at concentrations up to 100 μM. The sensitivity of response 8-bromo cyclic GMP and minoxidil and the cromakalin metabolite SQ 32,844 was similar in the two tissues.

Table II. Inhibition of spontaneous mechanical activity in rat portal vein by various vasodilators.

TABLE II

| Compound | $IC_{50}$ (μM)[a] |
|---|---|
| Cromakalim | 0.12 |
| Pinacidil | 0.15 |
| Nicorandil | 5.1 |
| Minoxidil | 150 |
| SQ 32,844 | 38 |
| Sodium nitroprusside | 0.042[b] |
| 8-Bromo cyclic GMP | 43 |

[a]Mean ± SEM of four cumulative concentration response curves for all agonists except cromakalim and pinacidil (n = 5).
[b]$IC_{50}$ taken at 50% of the maximum inhibition attained.

The test compounds, with the exception of sodium nitroprusside, reduced the frequency of twitches in a concentration dependent manner at approximately the same concentrations needed to reduce twitch height. Sodium nitroprusside increased twitch frequency with increasing concentration.

The spontaneous mechanical activity of the portal vein is thought to result from opening of voltage dependent calcium channels in response to depolarization associated with pacemakers. Thus, the portal vein provides a good model to investigate the influence of the hyperpolarization by the potassium channel activators on the voltage dependent channels. The inhibitory effects of the potassium channel activators involves a dose dependent reduction in twitch height with a concomitant reduction in twitch frequency. The decrease in force may be due to the hyperpolarizing influence of the potassium channel activators counteracting the depolarizing effect of the pacemakers, thereby leading to an effective blockade of the voltage dependent calcium channels. The hyperpolarization could also increase the time needed for the smooth muscle membranes to reach threshold, thus reducing the twitch frequency. Cromakalim, pinacidil, minoxidil, and sQ 32,844 exhibited similar potencies in the aorta and portal vein. The reduced potency of nicorandil, a potassium channel activator with nitrate properties, and sodium nitroprusside may indicate that quanylate cyclase plays a lesser role in relaxation of the portal vein than the aorta. Interestingly, sodium nitroprusside actually caused an increase in twitch frequency with the reduction in twitch height. 8-Bromo cyclic GMP, which bypasses the activation of guanylate cyclase, exhibited similar potency in the two blood vessels and reduced twitch frequency and height.

Conclusion: The inhibition of twitch height is an index of the potassium channel activating activity of the compounds tested.

Figure 2:
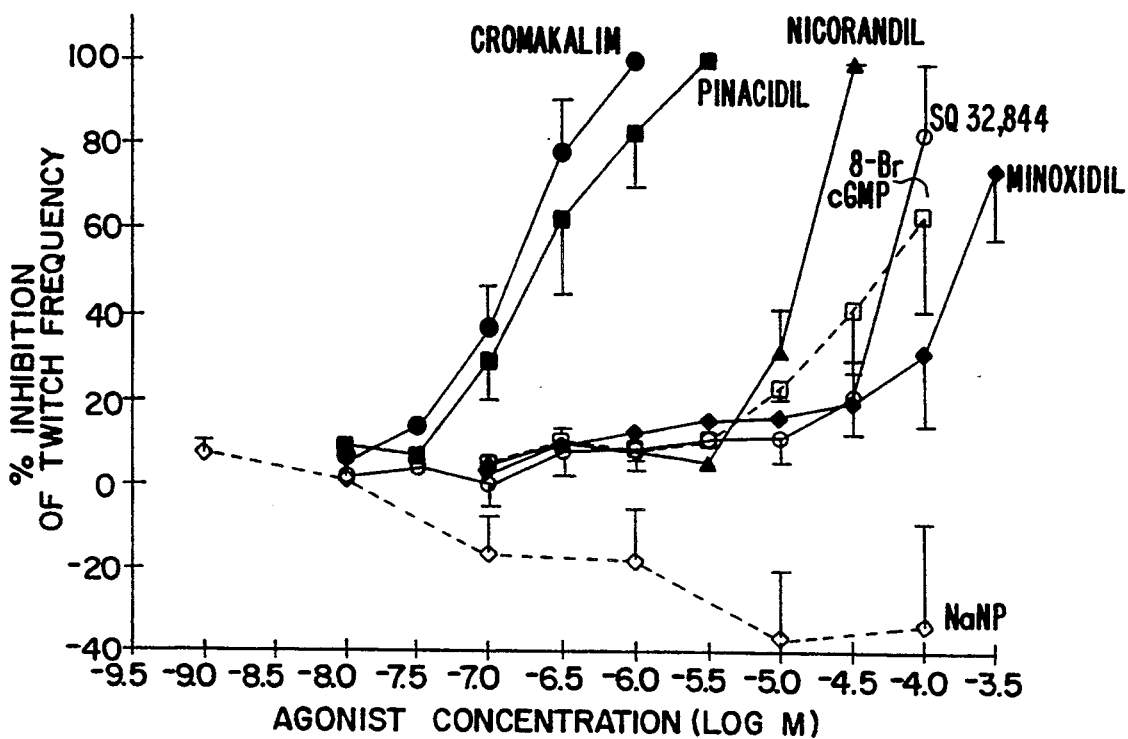
FIG. 2 is a graph of cumulative concentration response curves for affecting the frequency of spontaneous contractions.

FIG. 1 shows cumulative concentration response curves for inhibition of spontaneous force development in rat portal veins. Cromakalin (●) and pinacidil (■) were essentially equipotent followed by nicorandil (▲), 8-bromo cyclic GMP (□), SQ 32,844 (O), and minoxidil (◆). Sodium nitroprusside (◇) was incapable of inhibiting force development by more than 60% even at concentrations of 100 μM. FIG. 2 shows cumulative concentration response curves for affecting the frequency of the spontaneous contractions. Symbols are the same as for FIG. 1. With the exception of sodium nitroprusside, all the compounds decreased the frequency of the contractions in a concentration related fashion. Data are plotted as mean±SEM of 4 veins from individual rats.

For purposes of the present invention, potent potassium channel activators which may be employed in the method of the invention include cromakalim and pinacidil which have an $IC_{50}$ of less than 2 μM in the inhibition of spontaneous mechanical activity in rat portal vein and exclude nicorandil and minoxidil which have an $IC_{50}$ of 5.1 μM and 150 μM, respectively.

The following working Examples represent preferred embodiments of the present invention.

EXAMPLE 1

An injectable solution for use in administering pinacidil by intracoronary injection, by arterial angiography is produced as follows:

| Pinacidil | 50 mg |
|---|---|
| Methyl paraben | 5 mg |
| Propyl paraben | 1 mg |
| Sodium chloride | 25 g |
| Water for injection qs. | 5 l. |

The pinacidil, preservatives and sodium chloride are dissolved in 3 liters of water for injection and then the volume is brought up to 5 liters. The solution is filtered through a sterile filter and aseptically filled into presterilized vials which are then closed with presterilized rubber closures. Each vial contains a concentration of 75 mg of active ingredient per 150 ml of solution.

The above injectable is suitable for use in inhibiting myocardial necrosis and improving heart function during coronary occlusion and when administered during coronary occlusion and/or the reperfusion period.

EXAMPLE 2

A cardioplegic solution for use in inhibiting myocardial cell necrosis and improving myocardial function during ischemia and/or reperfusion is prepared as described in Example 1 except that the potassium channel activator employed is cromakalim.

EXAMPLE 3

The following experiment was conducted to determine the effect of pinacidil, cromakalim and nicorandil on myocardial cell necrosis and heart function during myocardial ischemia and reperfusion.

Method

For the determination of the effect of the potassium channel activators pinacidil and BRL 34915 (cromakalim) on post-ischemic necrosis and function, isolated, buffer perfused rat hearts were used. Male Sprague-Dawely rats (450-550 g) were used for all experiments. The rats were anesthetized using 30 mg/kg sodium pentobarbital (i.p.) They were intubated and then treated with i.v. heparin (1000 U/kg). While being mechanically ventilated, their hearts were perfused in situ via retrograde cannulation of the aorta. The hearts were then excised and quickly moved to a Langendorff apparatus where they were perfused with Krebs-Henseleit buffer (112 mM NaCl$_2$, 5 mM KCl, 1.2 mM MgSO$_4$, 1 mM KH$_2$PO$_4$, 1.25 mM CaCl$_2$, 11.5 mM dextrose and 2 mM pyruvate) (cardioplegic solution) at a constant pressure (80 MmHg). A saline-filled latex balloon attached to a metal cannula was then inserted into the left ventricle and connected to a Statham pressure transducer for measurement of left ventricular systolic and developed (LVDP) pressure. The hearts were allowed to equilibrate for 15 minutes at which time end diastolic pressure (EDP) was adjusted to 5 mm Hg and this was maintained for 5 minutes. Pre-ischemia, pre-drug function (HRXLVDP/1000), heart rate, and coronary blood flow (extracorporeal electromagnetic flow probe, Carolina Medical Electronics, King, N.C.) were then determined.

Once the baseline measurements were made, the hearts were divided into 4 groups (n=4-6 each): 1. Hearts receiving vehicle (cardioplegic solution). 2. Hearts receiving 1, 10 or 100 $\mu$M pinacidil (in cardioplegic solution). 3. Hearts receiving 1 or 7 $\mu$M BRL 34915 (in cardioplegic solution). 4. Hearts receiving 1, 10 or 100 $\mu$M nicorandil (in cardioplegic solution). Each heart received its respective treatment in the perfusion buffer for 10 minutes at which time functional and flow parameters were again measured. All hearts were then made globally ischemic by shutting off the perfusate for 25 minutes. Reperfusion was then instituted with the normal nondrug treated buffer. Reperfusion was maintained for 30 minutes at which time flow and functional parameters were again measured. Lactate dehydrogenase (LDH) release into the reperfusion effluent was measured and this is a measure of myocardial cell death or necrosis. The severity of ischemia was determined by the return of function during reperfusion, mitigation of contracture (lower end diastolic pressure) and LDH release.

Results

All of the compounds used have been shown to be potassium channel activators and have a ranked order of potency as follows: BRL 34915 > pinacidil > nicorandil. This is shown on FIGS. 1 and 2 where spontaneously contracting guinea pig portal veins are relaxed by the various potassium activators of interest. The inhibition of twitch height is an index of the potassium channel activating activity of these compounds.

At 1 and 100 $\mu$M concentration, pinacidil did not show any marked anti-ischemic activity and at the 100 $\mu$M dose, a tendency for toxic effects (before ischemia reduction in function) appeared. At the 10 $\mu$M concentration, pinacidil significantly improved post-ischemic cardiac function and reduced reperfusion end diastolic pressure (EDP) (contracture). These data are shown on FIG. 3a, 3b and 3c. At the doses used, pinacidil did not significantly reduce necrosis as measured by lactate dehydrogenase (LDH) release, however, it showed a tendency to do so. Nicorandil was not shown to be effective at any dose used and the data for 10 $\mu$M nicorandil are shown on FIG. 3. On FIG. 4a and 4b, similar data are shown for 7 $\mu$M cromakalim (BRL 34915). In this case, myocardial function was improved during reperfusion and LDH release and thus necrosis were reduced. Thus, the potent potassium channel activators pinacidil and cromakalim can reduce the severity of ischemia and improve post-ischemic recovery of function. This is important in patients undergoing coronary artery bypass and graft procedures as well as other methods of coronary recanalization. This is also important in patients undergoing episodes of transient ischemia as in many types of angina pectoris.

EXAMPLE 4

The following experiment was carried out to determine the relative efficacy of pinacidil and cromakalim in reducing infarct size in a model of 90 min of left circumflex coronary (LCX) occlusion and 5 hours of reperfusion in dogs. These compounds were administered directly into the ischemic coronary artery to determine direct cardioprotective effects thereof.

Determination of Canine Infarct Size

Mongrel dogs of either sex (10-15 kg) were anesthetized with intravenous sodium pentobarbital (30 mg/kg) and a catheter was placed into the right femoral artery for collection of blood samples. A Millar Mikrotip catheter pressure transducer was placed into the left femoral artery and was advanced into the aortic arch for the measurement of arterial blood pressure. An endotracheal tube was placed into the trachea and the animals were artificially respired such that eucapnia was maintained.

A left thoracotomy was performed at the fifth intercostal space and the heart was exposed. The left circumflex coronary (LCX) artery was isolated proximal to its first branch and a silk suture was placed around it for later occlusion. In all animals a bent 27 gauge needle with an attached catheter was inserted into the LCX distal to the occluder for intracoronary (i.c.) infusions of drug. A catheter was placed into the left atrial appendage for dye and radioactive microsphere injection.

The animals were allowed to stabilize for 5-10 minutes at which time an arterial blood sample was removed anaerobically for measurement of blood gases using a Radiometer (ABL3, Copenhagen) blood gas analyzer. Arterial blood pressure, heart rate and ECG were measured. At this time myocardial blood flow was measured using radioactive microspheres ($^{141}$Ce, $^{51}$Cr, $^{85}$Sr, or $^{46}$Sc; 15±3 $\mu$m, 3M Co.). Flow was measured using a reference flow technique (Dole, W. P. et al, "Relative error and variability in blood flow measurements with radiolabelled microspheres." *Am. J. Physiol.*, 1982; 243:H371-H378). All animals were subjected to LCX occlusion for 90 minutes. Before or during occlusion, the animals were divided into 6 groups: 1. Animals given pinacidil (0.09 $\mu$g/kg/min, LOWPIN i.c., n=6) starting 10 minutes before LCX occlusion. 2. Animals given pinacidil (0.9 μg/kg/min, HIGHPIN i.c., n=6). 3. Animals given cromakalim (0.1 μg/kg/min, CROM i.c., n=6) starting 10 minutes before LCX occlusion. 4. Vehicle control animals for groups 1,2 and 3 (n=8). 5. Animals given cromakalim (0.1 μg/kg/min, i.c., n=8) starting 2 minutes before reperfusion. 6. Vehicle controls for group 4 (n=7). The 0.1 and 0.09 μg/kg/min doses of cromakalim and pinacidil used were equimolar). Myocardial blood flows were again measured 10 minutes after drug administration (in groups 1-3) and at 40 minutes post-occlusion. At 90 minutes after occlusion, the LCX was reperfused. At 1 hour post-reperfusion, myocardial blood flow was again measured. The reperfusion was continued for a total of 5 hours at which time the LCX was cannulated and perfused at the animals' existing pressure with Ringer's lactate for determination of the area at risk. Patent blue violet dye (1 mg/kg of a 10 mg/ml solution) was injected into the left atrial catheter and the heart was quickly excised.

The atria were trimmed away leaving only the ventricles. The ventricles were then cut transversely into 0.5 cm slices. The borders of the area at risk (no dye) were delineated and separated and the slices were incubated at 37° C. for 30 minutes in a 1% solution of 2,3,5-triphenyl tetrazolium chloride in phosphate buffered saline. The ventricular slices were then dried and both sides were carefully traced onto clear transparencies. The area at risk and the infarcted region were demarcated on the transparencies. These tracings were transferred to paper and the areas of interest were measured using planimetric techniques. The infarct size was expressed as a percent of the left ventricular (LV) area at risk. Myocardial blood flow was calculated by taking myocardial pieces from the subepicardial and subendocardial halves of the ischemic and nonischemic regions of the left ventricular free wall. The radioactivity in the tissue pieces as well as the reference blood samples were determined in a Beckman Autogamma 8000 gamma counter and tissue flows were calculated from these counts.

Statistics

Changes in hemodynamic, blood flow, and infarct size variables were analyzed using an analysis of variance when more than two treatment groups were involved and a t-test when comparisons were made between two groups. Multiple comparisons were done using the Newman-Keuls test. all values are expressed as mean+SE.

Results

Infarct Size in Dogs

The hemodynamic data for the animals given i.c. cromakalim or pinacidil starting before LCX occlusion are shown on Table 1. As can be seen on Table 1, none of the drug treatments resulted in any significant changes in the hemodynamic status of the animals at any time measured. Neither LCX occlusion nor reperfusion resulted in any significant changes in blood pressure or heart rate in any of the treatment groups. Infarct sizes for drug treated and vehicle treated animals are shown in FIGS. 5a and 5b. The left ventricular areas at risk were similar in all groups. Infarct size as a percent of the left ventricular area at risk was significantly reduced in cromakalim treated animals, (25±5%) compared to vehicle controls (55±7%). Pinacidil in an equimolar dose did not affect infarct size, but a 10-fold higher dose did cause significant myocardial salvage to occur. Myocardial blood flows in these animals are shown in Table 2. Treatment with the potassium channel activators before ischemia did not significantly increase flow into the LCX region though this flow was slightly elevated. LCX occlusion reduced blood flow into the ischemic region to similar levels in all groups. The blood flow reduction was particularly marked in the subendocardial region. At 1 hour after the onset of reperfusion, flows into the formerly ischemic region returned to baseline values in vehicle controls. Cromakalim resulted in a significantly higher reflow into the subepicardial region at this time, though this was not observed in the subendocardium. Reflow in low dose pinacidil treated animals was not different from vehicle animals. High dose pinacidil did result in subepicardial reflows similar to those seen for cromakalim.

TABLE 1

The Effect of Intracoronary Pinacidil (0.09 or 0.90 μg/kg/min) or Cromakalim (0.10 μg/kg/min) on Hemodynamic Variables Before and After LCX Occlusion in Anesthetized Dogs

|  | Pre Drug | Post Drug | 40 min Post Occlusion | Min Post-Reperfusion | | | | |
|---|---|---|---|---|---|---|---|---|
|  |  |  |  | 60 | 120 | 180 | 240 | 300 |
| Systolic Blood Pressure (mmHg) | | | | | | | | |
| Vehicle (n = 8) | 124 ± 8 | 120 ± 10 | 112 ± 7 | 102 ± 5 | 112 ± 7 | 124 ± 9 | 113 ± 10 | 122 ± 8 |
| Low Dose Pinacidil (n = 6) | 114 ± 6 | 119 ± 4 | 105 ± 5 | 98 ± 8 | 103 ± 8 | 104 ± 5 | 104 ± 7 | 110 ± 6 |
| High Dose Pinacidil (n = 6) | 135 ± 6 | 133 ± 7 | 119 ± 8 | 116 ± 7 | 121 ± 8 | 112 ± 8 | 114 ± 9 | 115 ± 9 |
| Cromakalim (n = 6) | 135 ± 8 | 135 ± 6 | 116 ± 4 | 123 ± 6 | 124 ± 6 | 119 ± 5 | 117 ± 5 | 121 ± 8 |
| Diastolic Blood Pressure (mmHg) | | | | | | | | |
| Vehicle (n = 8) | 96 ± 5 | 92 ± 8 | 92 ± 7 | 83 ± 7 | 84 ± 7 | 97 ± 7 | 96 ± 8 | 88 ± 8 |
| Low Dose Pinacidil (n = 6) | 95 ± 5 | 87 ± 6 | 86 ± 6 | 92 ± 9 | 82 ± 6 | 82 ± 6 | 84 ± 5 | 85 ± 6 |
| High Dose Pinacidil (n = 6) | 118 ± 7 | 103 ± 5 | 94 ± 7 | 85 ± 7 | 90 ± 8 | 87 ± 7 | 84 ± 6 | 90 ± 7 |
| Cromakalim (n = 6) | 113 ± 6 | 113 ± 4 | 99 ± 4 | 105 ± 7 | 103 ± 7 | 97 ± 6 | 95 ± 7 | 98 ± 9 |
| Heart Rate (beats/min) | | | | | | | | |
| Vehicle (n = 8) | 161 ± 6 | 163 ± 6 | 158 ± 6 | 153 ± 6 | 162 ± 8 | 164 ± 10 | 167 ± 10 | 160 ± 14 |
| Low Dose Pinacidil (n = 6) | 146 ± 15 | 148 ± 15 | 153 ± 12 | 147 ± 17 | 139 ± 17 | 152 ± 12 | 150 ± 13 | 154 ± 12 |
| High Dose Pinacidil (n = 6) | 150 ± 13 | 152 ± 15 | 140 ± 11 | 140 ± 9 | 142 ± 11 | 145 ± 12 | 147 ± 14 | 152 ± 11 |
| Cromakalim (n = 6) | 163 ± 6 | 162 ± 4 | 156 ± 5 | 153 ± 7 | 155 ± 6 | 162 ± 4 | 164 ± 5 | 154 ± 4 |

All values are mean ± SE

TABLE 2

The Effect of Intracoronary Pinacidil (0.09 or 0.90 µg/kg/min) or Cromakalim (0.10 µg/kg/min) on Regional Myocardial Blood Flow Before and After LCX Occlusion in Anesthetized Dogs

| | Non Occluded Region | | | | Occluded Region | | | |
|---|---|---|---|---|---|---|---|---|
| | Pre Drug | Post Drug | 40 min occl | 1 hr reperf | Pre Drug | Post Drug | 40 min occl | 1 hr reperf |
| Subepicardium | | | | | | | | |
| Vehicle (n = 8) | 91 ± 9 | 82 ± 7 | 105 ± 11 | 99 ± 8 | 79 ± 8 | 85 ± 10 | 17 ± 3[a] | 87 ± 14 |
| Low Dose Pinacidil (n = 6) | 79 ± 13 | 95 ± 30 | 101 ± 14 | 99 ± 20 | 78 ± 20 | 91 ± 22 | 16 ± 8[a] | 77 ± 11 |
| High Dose Pinacidil (n = 6) | 103 ± 13 | 90 ± 14 | 100 ± 12 | 86 ± 10 | 76 ± 12 | 138 ± 30 | 21 ± 6[a] | 194 ± 60 |
| Cromakalim (n = 6) | 97 ± 14 | 80 ± 7 | 138 ± 13 | 139 ± 3 | 86 ± 5 | 142 ± 55 | 25 ± 7[a] | 208 ± 29[a,b] |
| Subendocardium | | | | | | | | |
| Vehicle (n = 8) | 100 ± 9 | 80 ± 6 | 111 ± 10 | 103 ± 5 | 75 ± 7 | 80 ± 6 | 5 ± 2[a] | 99 ± 14 |
| Low Dose Pinacidil (n = 6) | 70 ± 10 | 79 ± 21 | 98 ± 12 | 90 ± 10 | 91 ± 20 | 85 ± 26 | 3 ± 2[a] | 104 ± 30 |
| High Dose Pinacidil (n = 6) | 98 ± 13 | 80 ± 10 | 107 ± 9 | 89 ± 10 | 77 ± 12 | 77 ± 9 | 8 ± 3[a] | 153 ± 40 |
| Cromakalim (n = 6) | 100 ± 5 | 81 ± 12 | 139 ± 9 | 126 ± 7 | 91 ± 8 | 76 ± 24 | 8 ± 3[a] | 127 ± 7 |

All values are mean ± SE.
[a] Significantly different from its respective pre-drug value (p<0.05).
[b] Significantly different from its respective saline value (p<0.05).

It has been previously shown that the potassium channel activators pinacidil and cromakalim have direct myocardial protective effects in a model of global ischemia and reperfusion in isolated buffer perfused rat hearts (Grover, G. J., et al, "Coronary vasodilator and cardiac functional effects of the potassium channel activator cromakalim in ischemic and nonischemic rat and gunea pig hearts." *The Physiologist* 1988; 31:A150 and Flaim, S. F., et al, "Effect of pinacidil on coronary flow and function in isolated perfused rat or guinea pig hearts during ischemic or nonischemic conditions." *The Physiologist* 1988; 31:A149). This concept was tested in the isolated heart to avoid the alterations in peripheral hemodynamics and possible coronary steal which may occur with general vasodilators such as these. Both pinacidil (a cyanoguanidine analog) and cromakalim (a benzopyran analog) resulted in improvements in repefusion function in the isolated rat heart though cromakalim was more effective at reducing LDH release (Grover et al, supra and Flaim et al, supra). It appears that beneficial effects of these compounds on function and enzyme release are related to potassium channel activation in some way as the ATP-sensitive potassium channel blocker glyburide (glybenclamide) (Fosset, M., et al, "Sulfonylureas control action potential properties in heart cells via high affinity receptor that are linked to ATP-dependent K+channels." *J. Biol. Chem.* 1988; 263:7933–7936, Schmid-Antomarchi, H, et al, "The receptor for antidiabetic sulfonylureas controls the activity of the ATP-modulated K+channel in insulin-secreting cells." *J. Biol. Chem.* 1987; 262:15840–15844). (12, 13) was found to completely reverse the protective effects of these compounds.

Imai, N., et al, "Comparative effects of nitroprusside and pinacidil on myocardial blood flow and infarct size in awake dogs with acute myocardial infarction." *Circulation* 1988; 7:705–711, reported showing that i.v. pinacidil in doses resulting in peripheral and coronary vasodilation does not reduce infarct size in a canine model of occlusion and reperfusion. It may be difficult to interpret the results as the peripheral effects of the i.v. treatment may have masked the direct myocardial protective effects of pinacidil. Thus, to determine if the cardioprotective effects of cromakalim and pinacidil on myocardial necrosis observed in vitro could also be seen in vivo, these drugs were infused directly into the ischemic and reperfused region. For the purpose of comparison, equimolar doses of cromakalim and pinacidil were infused in the affected coronary artery. It was found that while cromakalim significantly reduced infarct size, pinacidil did not have any significant effect at the lower (equimolar) dose. At the higher dose, pinacidil did significantly reduce infarct size.

EXAMPLE 5

The following experiment was carried out to determine the effect of intracoronary and intravenous cromakalim on infarct size, myocardial cell necrosis and heart function during myocardial ischemia and reperfusion.

METHODS

Mongrel dogs of either sex (10–15 kg) were anesthetized with intravenous sodium pentabarbital (30 mg/kg) and a catheter was placed into the right femoral artery for collection of blood samples. A Millar Mikrotip catheter pressure transducer was placed into the left femoral artery and was advanced into the aortic arch for the measurement of arterial blood pressure. An endotracheal tube was placed into the trachea and the animals were artificially respired such that eucapnia was maintained.

A left thoracotomy was performed at the fifth intercostal space and the heart was exposed. The LCX was isolated proximal to its first branch and a silk suture was placed around it for later occlusion. A catheter was placed into the left atrial appendage for dye and radioactive microsphere injection.

The animals were allowed to stabilize for 5–10 minutes at which time an arterial blood sample was removed anaerobically for measurement of blood gases using a Radiometer (ABL3, Copenhagen) blood gas analyzer. Arterial blood pressure, heart rate and ECG were measured. At this time myocardial blood flow was measured using radioactive microspheres ($^{141}$Ce, $^{51}$Cr, $^{85}$Sr, or $^{46}$Sc; 15+3 Nm, 3M Co.). A study was done to determine if i.v. cromakalim can be successfully given systemically in doses which lower infarct size. Doses of cromakalim of 100 µg/kg/min down to 0.5 µg/kg/min were tried and it was found that the highest dose which did not result in heart failure secondary to a compromised coronary perfusion pressure when given i.v. during ischemia was 0.5 µg/kg/min. Thus experiments were carried out to determine whether i.v. cromakalim at this dose (n=9) or vehicle (n=10) could reduce infarct size in the model described above.

The reperfusion was continued for a total of 5 hours at which time the LCX was cannulated and perfused at the animals' existing pressure with Ringer's lactate for determination of the area at risk. Patent blue violet dye (1 mg/kg of a 10 mg/mL solution) was injected into the left atrial catheter and the heart was quickly excised. The atria were trimmed away leaving only the ventricles. The ventricles were then cut transversely into 0.5 cm slices. The borders of the area at risk (no dye) were delineated and separated and the slices were incubated at 37° C. for 30 minutes in a 1% solution of 2,3,5-triphenyl tetrazolium chloride in phosphate buffered saline. The ventricular slices were then dried and both sides were carefully traced onto clear transparencies. The area at risk and the infarcted region were demarcated on the transparencies. These tracings were transferred to paper and the areas of interest were measured using planimetric techniques. The infarct size was expressed as a percent of the left ventricular (LV) area at risk. Myocardial blood flow was calculated by taking myocardial pieces from the subepicardial and subendocardial halves of the ischemic and nonischemic regions of the left ventricular free wall. The radioactivity in the tissue pieces as well as the reference blood samples were determined in a Beckman Autogamma 8000 gamma counter and tissue flows were calculated from these counts.

Statistics

Changes in hemodynamic, blood flow, and infarct size variables were analyzed using an analysis of variance. Multiple comparisons were done using the Newman-Keuls test. When only two groups were compared, a t-test was used. All values are expressed as mean±SE.

RESULTS

Cromakalim was given i.v. in a dose of 100 µg/kg/min and caused profound hypotension which resulted in rapid death of the animals upon occlusion of the LCX. The dose of cromakalim was then reduced until the blood pressure was maintained during occlusion and reperfusion. The highest dose tested which did not significantly reduce blood pressure under these conditions was found to be 0.5 µg/kg/min. The hemodynamic data for these animals are shown in Table 3 and the regional myocardial blood flow data are shown in Table 4. As shown in FIGS. 6a and 6b, this dose of cromakalim did not significantly reduce infarct size when expressed as a percent of the area at risk. This dose of cromakalim had no significant effect on collateral blood flow, but did significantly increase reflow at 1 hour, particularly in the subepicardial region. Cromakalim did not effect flow into nonischemic region before and during LCX occlusion, but significantly increased it during reperfusion. This effect was greater once again in the subepicardial region.

DISCUSSION

Cromakalim has been shown to reduce infarct size when given by the intracoronary route (I.C.), but when an equivalent dose is given i.v., the animals rapidly progress into cardiac failure once the LCX is occluded. The i.v. dose of cromakalim was drastically reduced in order to maintain hemodynamic stability during occlusion. The highest dose in which this was achieved was the 0.5 µg/kg/min dose and it was found that this was not sufficient to reduce infarct size.

TABLE 3

The effect of i.v. (0.6 µg/kg/min) Cromakalim on Hemodynamic Variables Before and After Myocardial Ischemia.

| | Preocclusion | | 40 min | Reperfusion | | |
|---|---|---|---|---|---|---|
| | Pre Drug | Post-Drug | Post Occlusion | 1 hr | 3 hr | 5 hr |
| Systolic Blood Pressure (mmHg) | | | | | | |
| Vehicle | 149 ± 6 | 137 ± 7 | 121 ± 6$^a$ | 121 ± 5$^a$ | 115 ± 7$^a$ | 109 ± 7$^a$ |
| Cromakalim | 148 ± 8 | 141 ± 6 | 120 ± 5$^a$ | 115 ± 6$^a$ | 117 ± 8$^a$ | 120 ± 6$^a$ |
| Diastolic Blood Pressure (mmHg) | | | | | | |
| Vehicle | 121 ± 5 | 115 ± 6 | 96 ± 6$^a$ | 92 ± 6$^a$ | 85 ± 8$^a$ | 81 ± 6$^a$ |
| Cromakalim | 120 ± 6 | 108 ± 6 | 86 ± 6$^a$ | 84 ± 6$^a$ | 85 ± 9$^a$ | 88 ± 5$^a$ |
| Heart Rate (beats/min) | | | | | | |
| Vehicle | 181 ± 10 | 178 ± 9 | 157 ± 7 | 155 ± 8 | 161 ± 6 | 168 ± 4 |
| Cromakalim | 172 ± 6 | 167 ± 6 | 163 ± 6 | 179 ± 6 | 172 ± 5 | 166 ± 7 |
| Ectopic Beats (beats/min) | | | | | | |
| Vehicle | — | — | — | 66 ± 22 | 88 ± 25 | 123 ± 35 |
| Cromakalim | — | — | — | 30 ± 14 | 74 ± 28 | 135 ± 63 |

All values are mean ± SE.
$^a$Significantly different from its respective predrug value (p<0.05).

TABLE 4

The Effect of i.v. (0.5 µg/kg/min) Cromakalin on Regional Myocardial Blood Flow Before and After Myocardial Ischemia.

| | Nonoccluded Rerion | | | Occluded Region | | |
|---|---|---|---|---|---|---|
| | Pre-Occl | 40 min Post-Occl | 1 hr Reperfusion | Pre-Occl | 40 min Post-Occl | 1 hr Reperfusion |
| Subepicardium | | | | | | |
| Vehicle | 85 ± 9 | 101 ± 7 | 100 ± 11 | 83 ± 8 | 17 ± 4$^a$ | 88 ± 11 |
| Cromakalim | 88 ± 12 | 130 ± 12 | 253 ± 35$^{a,b}$ | 86 ± 9 | 16 ± 3$^a$ | 320 ± 50$^{a,b}$ |
| Subendocardium | | | | | | |
| Cehicle | 107 ± 15 | 100 ± 7 | 124 ± 18 | 98 ± 10 | 3 ± 1$^a$ | 94 ± 11 |

TABLE 4-continued

The Effect of i.v. (0.5 µg/kg/min) Cromakalin on Regional Myocardial Blood Flow Before and After Myocardial Ischemia.

| | Nonoccluded Rerion | | | Occluded Region | | |
|---|---|---|---|---|---|---|
| | Pre-Occl | 40 min Post-Occl | 1 hr Reperfusion | Pre-Occl | 40 min Post-Occl | 1 hr Reperfusion |
| Cromakalim | 97 ± 17 | 116 ± 12 | 214 ± 31$^{a,b}$ | 97 ± 11 | 3 ± 2$^a$ | 179 ± 49 |

All values are mean ± SE.
$^a$Significantly different from its respective preocclusion value ($p<0.05$).
$^b$Significantly different from its respective vehicle control value ($p<0.05$).

What is claimed is:

1. A method of inhibiting myocardial cell necrosis and improving myocardial function during myocardial ischemia and/or reperfusion in a mammalian species, which comprises locally administering to the heart of a mammalian species in need of such treatment an effective amount of a potent potassium channel activator which is pinacidil in the range of from about 0.001 to about 30 mg/kg per treatment, to reduce or eliminate myocardial cell necrosis, ischemia injury and/or reperfusion injury, wherein the potent potassium channel activator exhibits potent inhibition of spontaneous mechanical activity in rat portal vein and has an IC$_{50}$ of less than about 2 µM.

2. The method as defined in claim 1 wherein the potent potassium channel activator is locally administered to the heart by arterial angiography, by intracoronary injection, or in a cardioplegic solution by the aortic route.

3. The method as defined in claim 1 wherein the potent potassium channel activator is administered in a cardioplegic solution.

4. The method as defined in claim 1 wherein the potent potassium channel activator is administered before or during coronary occlusion or coronary occlusion and reperfusion.

5. The method as defined in claim 1 wherein the potent potassium channel activator is administered only during reperfusion.

6. The method as defined in claim 1 wherein the potent potassium channel activator exhibits potent inhibition of spontaneous mechanical activity in rat portal vein and has an IC$_{50}$ of less than about 2 µM.

7. The method as defined in claim 1 wherein the pinacidil is administered in an amount of from about 0.5 to about 25 mg/kg/treatment.

* * * * *